(12) United States Patent
Axelson, Jr. et al.

(10) Patent No.: US 7,686,812 B2
(45) Date of Patent: Mar. 30, 2010

(54) METHOD FOR SETTING THE ROTATIONAL POSITION OF A FEMORAL COMPONENT

(75) Inventors: Stuart L. Axelson, Jr., Succasunna, NJ (US); Jerry D'Alessio, II, Belleville, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 708 days.

(21) Appl. No.: 11/478,789

(22) Filed: Jun. 30, 2006

(65) Prior Publication Data

US 2008/0004701 A1 Jan. 3, 2008

(51) Int. Cl.
*A61B 17/58* (2006.01)
*A61B 17/60* (2006.01)
*A61F 2/00* (2006.01)

(52) U.S. Cl. .................. 606/88; 606/86 R; 623/20.14; 623/20.16

(58) Field of Classification Search .................. 606/79, 606/82, 86 R, 87–89; 623/16.11, 18.11, 623/20.12, 20.14, 20.35, 22.11, 20.11, 20.13
See application file for complete search history.

(56) References Cited

U.S. PATENT DOCUMENTS

| | | | |
|---|---|---|---|
| 4,501,266 A | 2/1985 | McDaniel | |
| 4,738,254 A | 4/1988 | Buechel et al. | |
| 5,314,482 A | 5/1994 | Goodfellow et al. | |
| 5,486,178 A * | 1/1996 | Hodge | 606/82 |
| 5,540,696 A | 7/1996 | Booth, Jr. et al. | |
| 5,549,689 A * | 8/1996 | Epstein et al. | 623/20.23 |
| 5,597,379 A * | 1/1997 | Haines et al. | 606/80 |
| 5,733,292 A | 3/1998 | Gustilo et al. | |
| 5,800,438 A | 9/1998 | Tuke et al. | |
| 5,860,980 A | 1/1999 | Axelson, Jr. et al. | |
| 5,879,354 A | 3/1999 | Haines et al. | |
| 5,911,723 A | 6/1999 | Ashby et al. | |
| 6,022,377 A | 2/2000 | Nuelle et al. | |
| 6,197,064 B1 | 3/2001 | Haines et al. | |
| 6,458,135 B1 * | 10/2002 | Harwin et al. | 606/88 |
| 6,575,960 B2 | 6/2003 | Becker et al. | |

(Continued)

OTHER PUBLICATIONS

Achieve Dynamic Balance (1 page).

(Continued)

*Primary Examiner*—Thomas C Barrett
*Assistant Examiner*—Larry E Waggle, Jr.
(74) *Attorney, Agent, or Firm*—Lerner, David, Littenberg, Krumholz & Mentlik, LLP

(57) ABSTRACT

A method for setting the internal-external rotational position of a prosthetic femoral component with respect to the tibial comprises: forming a cylindrical surface on the posterior femoral condyles. The cylindrical surface is formed about an axis extending in a proximal distal direction with respect to the femur. A template is placed on the distal femur which has a cylindrical guide surface for engaging the posterior femoral condyles. When placed against a planar resected surface of the distal femur the guide surfaces contact the cylindrically shaped posterior condyles. The template is rotated on the cylindrical guide surface as the knee joint is moved from flexion to extension until the template cylindrical guide surfaces are in a position with respect to the tibial condyle surfaces to properly balance the knee ligaments.

16 Claims, 13 Drawing Sheets

U.S. PATENT DOCUMENTS

| | | | |
|---|---|---|---|
| 7,442,196 B2 * | 10/2008 | Fisher et al. | 606/88 |
| 2003/0187452 A1 | 10/2003 | Smith et al. | |
| 2005/0177169 A1 * | 8/2005 | Fisher et al. | 606/88 |
| 2005/0177170 A1 | 8/2005 | Fisher et al. | |
| 2005/0267485 A1 * | 12/2005 | Cordes et al. | 606/88 |
| 2006/0122616 A1 * | 6/2006 | Bennett et al. | 606/87 |

OTHER PUBLICATIONS

Christopher W. Olcott, MD and Richard D. Scott, MD, A Comparison of 4 Intraoperative Methods to Determine Femoral Component Rotation During total Knee Arthroplasty, The Journal of Arthroplasty, 2000; 15[1]:22-26.

Libra Dynamic Knee Balancer (1 page).

* cited by examiner

METHOD FOR SETTING THE ROTATIONAL POSITION OF A FEMORAL COMPONENT

BACKGROUND OF THE INVENTION

The present invention relates generally to a femoral component having curved or radially shaped anterior surface of the posterior condyles and instruments for use in implanting the same and more particularly for instruments for use in balancing the ligaments extending between the femur and tibia.

Structures that made up the knee joint include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament, and the lateral collateral ligament. In an arthritic knee, protective cartilage at the point of articulation of the femur with the tibia has been worn away to allow the femur to directly contact the tibia. This bone-on-bone contact causes significant pain and discomfort. The primary goals of a knee procedure are to replace the distal end of the femur, the proximal end of the tibia, and often the inner surface of the patella with prosthetic parts to avoid bone-on-bone contact and provide smooth, well-aligned surfaces for joint movement, while also creating a stable knee joint that moves through a wide range of motion.

One of the challenges in knee surgery is to properly balance ligament tension, especially in the medial and lateral collateral ligaments, through a full range of motion of the knee. The collateral ligaments, which connect the distal femur and proximal tibia on the medial and lateral aspects of the knee, account for much of the stability of the knee. If one of the collateral ligaments is too lax or too tight relative to the other collateral ligament, the knee will typically be unstable, range of motion may be limited, the patella may track improperly, and the femur and/or tibia may wear unevenly, leading to arthritis and pain. Uneven ligament tension after knee surgery will typically cause joint instability and poor patellar tracking, limited range of motion, and impaired function of the knee, as well as uneven, increased wear of the prosthetic device, which often necessitates repeat surgery. Thus, it is imperative for the short and long-term success of a knee procedure to achieve balanced ligament tension in the knee through a full range of motion.

The components of a total knee prosthesis may be selected and positioned to balance ligament tension. Since the femoral and tibial components of the prosthesis are attached to cut surfaces of the distal femur and proximal tibia respectively, placement and orientation of the bone cuts are also critically important. Typically, the tibial component of the prosthesis is positioned on a flat, horizontal cut surface of the proximal tibia (at a 90 degree angle relative to the long axis of the tibia), and the position and orientation of the tibial component typically do not vary greatly from knee to knee. Therefore, most of the variation in positioning of the total knee prosthesis typically occurs in positioning the femoral component and the femoral bone cuts. The surgeon makes these femoral bone cuts to achieve a position and orientation of the femoral prosthetic component so as to optimally balance ligament tension through a full range of motion of the knee.

SUMMARY OF THE INVENTION

Alignment of total knee replacements is achieved through several methods, including extramedullary, intramedullary, and computer navigation. When it comes to rotational alignment of the prosthesis in the transverse plan (i.e. internal/external rotation) several methods are currently utilized to achieve the "correct" rotation. They are as follows:

a) Anatomic landmarks such as the transepicondylar axis, femoral anterior-posterior axis line and the poster condylar axis.

b) Spacer blocks or shims to balance and place the components via rotation based on the tibial resection. (see U.S. Pat. No. 4,738,254).

c) Instruments that reference the posterior/intact condyles to rotate or "jack" the femur by rotating about the medial or lateral condyle until the ligaments are tensioned properly (see U.S. Patent Publication US 2005/0177169 A1).

The present invention helps surgeons to accomplish the correct rotational alignment by allowing the femoral trial to rotate via a radial arc created on the posterior condyles in flexion. The knee can be taken through a range of motion, and the trial will self-adjust to the correct rotation without the need to provide secondary mechanical methods to adjust or torque the knee. Gap balancing is accomplished by changing the thickness of the insert to provide the proper balance between the flexion and extension space.

The femoral tibial components may be of a tricompartmental design, unicompartmental, or bicompartmental design.

In most total knee replacement systems currently available rotation of the femoral component about the long axis of the femur is "locked in" when the posterior condyles are resected and rotation and medial-lateral translation of the femoral component are adjusted independently. In the present invention the femoral implant and trial the rotation of the femoral component can be adjusted after the posterior condyles are resected since the condyles are resected in an arc rather than planar. Possible disadvantages of this approach include (1) more bone may be removed by the radial posterior cut than would be removed by a planar posterior cut and (2) rotation and medial-lateral translation of the femoral component about the end of the femur are linked by the arc of the radial cut and cannot be adjusted independently.

In most total knee replacement systems, the tibial bone resection is made at 90 degrees to the axis of the tibia. In most knees with a "normal" anatomy, if the tibial resection is at 90 degrees the femoral component will need to be placed in 3 degrees of external rotation on average about the long axis of the femur in order for the knee replacement system to function properly. The proper amount of external rotation for any particular knee replacement will, of course, depend on the individual anatomy of the patient.

Anatomical landmarks provide reference points, but are known to produce inconsistencies among patients with anatomic variations, hypoplastic deformities or laxity of the collateral ligaments. Also, with minimally invasive surgical (MIS) techniques on the rise, the ability to visualize and assess the lateral epicondyle is difficult, if not impossible. The transepicondylar axis is believed to be a more reproducible landmark, however, it can still introduce error when attempting to create a symmetric flexion gap. Finally, the posterior femoral axis has been used to generally externally rotate the femoral implant 3 degrees to develop a symmetric flexion gap assuming that the tibial component is cut in 90° with respect to the mechanical axis, however, it does not pay much attention to the relationship between resection planes and soft tissue structures during gait.

While mechanical spacer blocks or positioners allow the knee rotation to be balanced by aligning the cutting guides with the tibial resection while tensioning the ligaments, however, they do not allow for a dynamic assessment to be accomplished prior to locking in femoral rotation. By using a mechanism to torque the knee about either the medial or lateral point via a mechanical device, the surgeon could over tighten the device and provide too much rotation.

DETAILED DESCRIPTION

Figure 1:
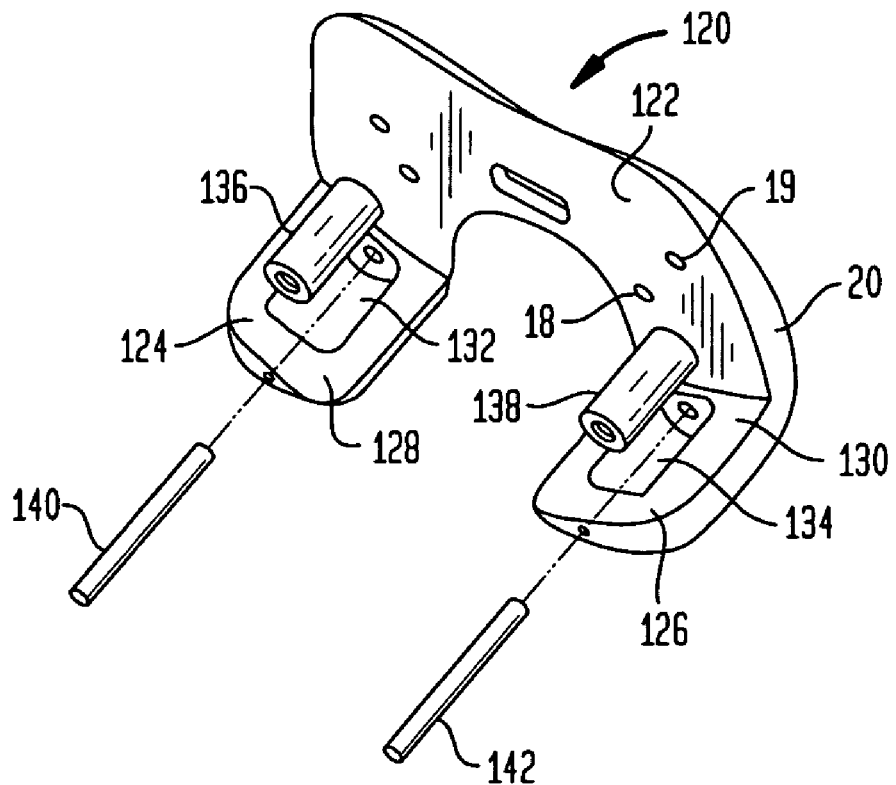
FIG. 1 is an exploded isometric view of the rotational alignment guide of the present invention.
Figure 2:
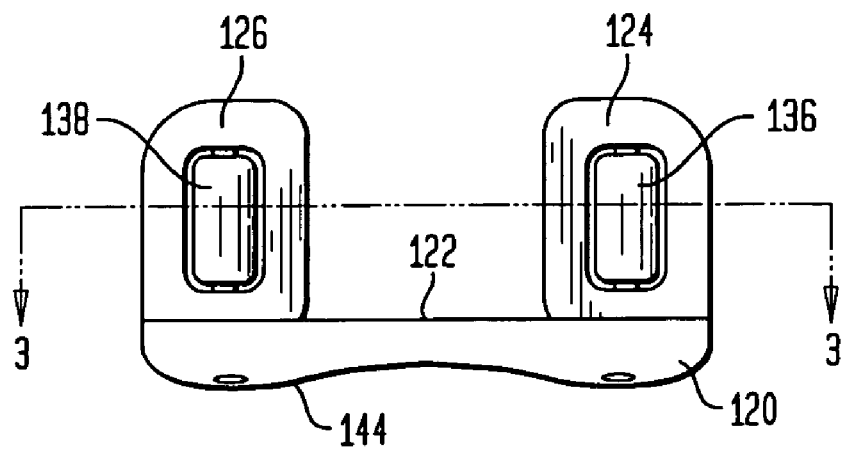
FIG. 2 is a top view of an assembled alignment guide as shown in FIG. 1.
Figure 3:
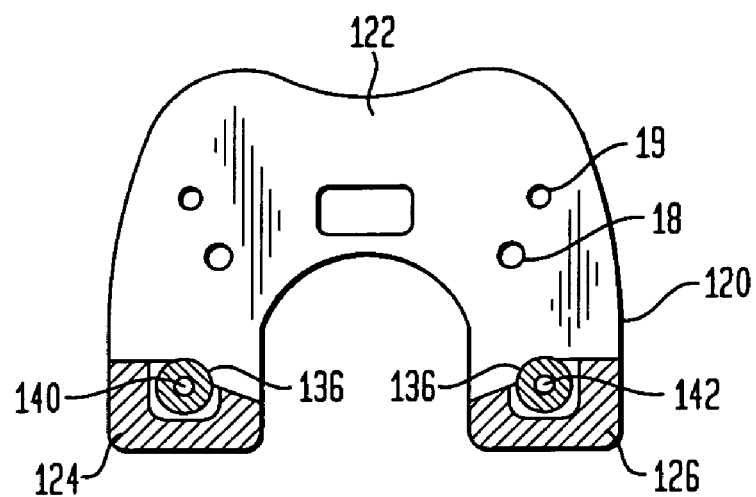
FIG. 3 is a partial cross-sectional view along lines 3-3 of FIG. 2.
Figure 4:
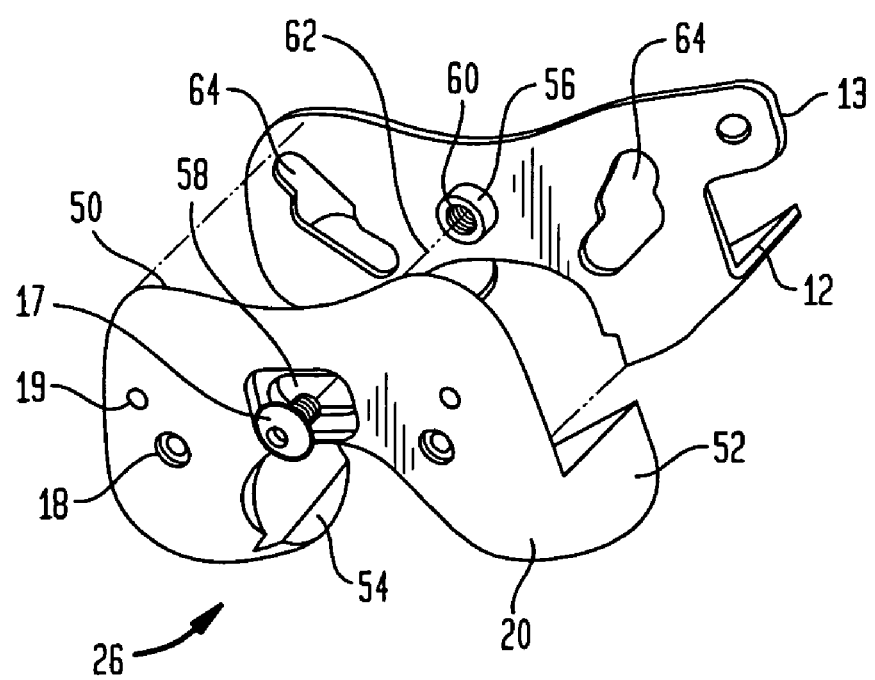
FIG. 4 is an exploded view of a second embodiment of the present invention when viewed from the distal end.

Referring to FIGS. 1-3, there is a first preferred one-piece embodiment of a femoral trial assembly generally denoted as 120. Femoral trial 120 includes a proximally facing surface 122 for contacting the resected distal surface of a femur. The femoral trial 120 has a pair of posterior condyles 124 and 126 which have curved anteriorly facing surfaces 128 and 130 respectively. The curved surfaces 128 and 130 are cylindrical surfaces each having a radius of 1.9 to 4 inches with a center located on or slightly offset from the center line of the distal femur. In the preferred embodiment a pair of recesses 132 and 134 are formed in the anterior surfaces 128 and 130 to receive roller bearings 136 and 138. Bearings 136 and 138 are held within recesses 130 and 132 by pins 140 and 142. Pins 140 and 142 provides the axes of rotation about which roller bearings 136 and 138 rotate. Surface 122 has a plurality of pin holes 19 therethrough to receive bone pins for mounting the trial on the distal femur. Two holes 18 are also provided so that a resection guide may be pinned thereon to make the anterior or posterior chamfer cuts typically associated with a femoral component of a knee replacement.

Referring to FIG. 2, there is shown a top view of the preferred trial component of FIG. 1 which shows the trial bearing surface 144 of the trial component. Referring to FIG. 3, there is shown a partial cross sectional view showing a cross section through the posterior condylar surfaces 124 and 126 of the trial component 120 including roller bearings 136 and 138 mounted on pins 140 and 142 respectively.

Figure 5:
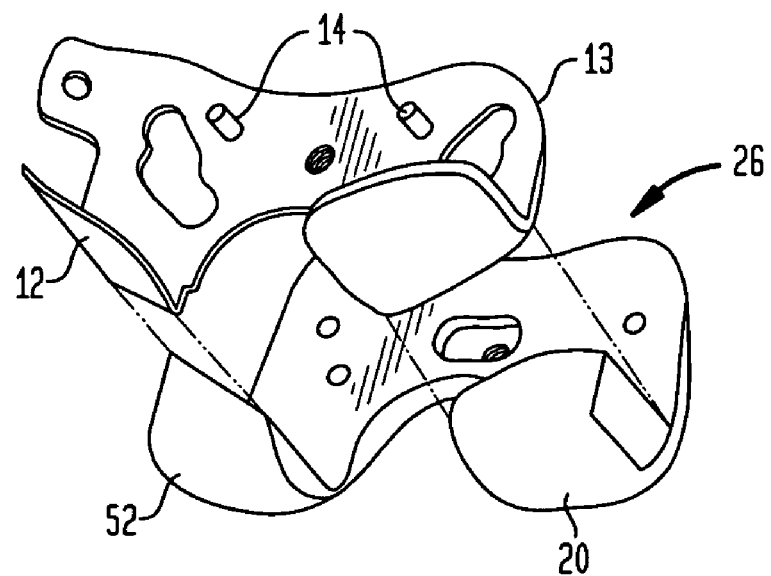
FIG. 5 is an exploded isometric view of the second embodiment of the present invention viewed from the proximally facing side when implanted.
Figure 6:
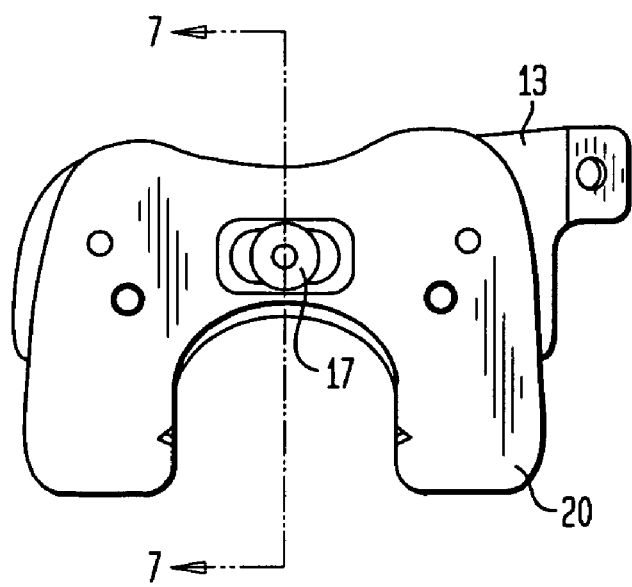
FIG. 6 is an assembled view of the alignment guide of the present invention from the distal facing side.
Figure 7:
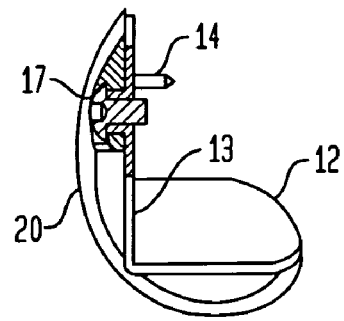
FIG. 7 is a cross-sectional view of the assembled second embodiment shown in FIG. 6 along lines 7-7.

Referring to FIGS. 4-7, there is shown an alternate embodiment of the femoral trial in the form of a two-piece femoral trial assembly 26. Trial 26 includes a body 20 with bone pin holes 18 and 19 extending therethrough. Instead of rotating on bearings 136, 138 the trial body 20 rotates on a plate 13 attached to the distal femur. The distal side 50 of body 20 includes proximally extending posterior portions 52 and 54 respectively. Rotatably mounted on body 20 is a shim plate 13 which has a bearing element 56 which engages a slot 58 in body 20. A screw 17 is provided to engage a threaded bore 60 of element 56 so that body 20 may be rotated about axis 62 after the curved posterior plates 12 are engaged on a resected posterior condyle of the femur. Other options for attaching the shim plate 13 to the trial body 20 could be rivets or welded pins. Shim plate 13 includes a pair of slots 64 for providing clearance for the bone pins extending through bores 19 and body 20 so that body 20 can be fixed to the bone prior to drilling locating holes through bore 18. Slot 64 are shaped to allow adequate rotation for the purposes of setting internal and external rotation of the femoral component. As shown in FIG. 5, shim plate 13 includes a pair of proximally extending locking pins 14 which initially secure the assembled trial component 26 to the resected distal femur.

Figure 8:
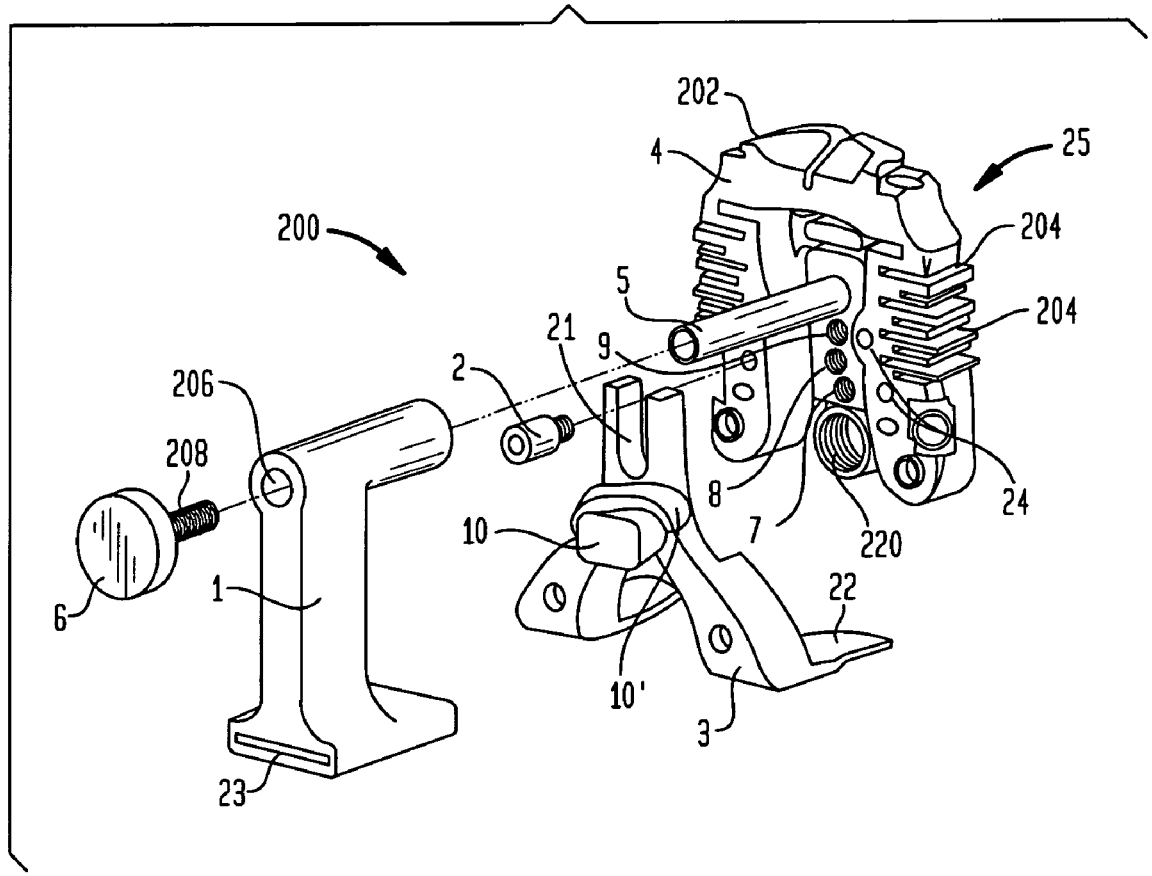
FIG. 8 is an exploded isometric view of an instrument used to resect the posterior condyles in connection with the alignment guide of the present invention.
Figure 9:
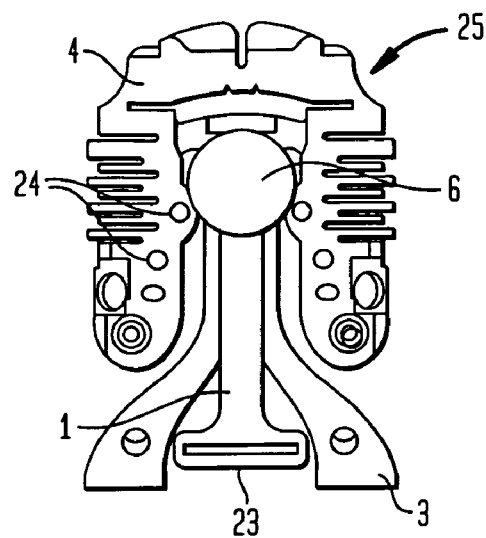
FIG. 9 is a distal view of an assembled instrument of FIG. 8.

Referring to FIGS. 8 and 9, in the preferred method after the proximal tibia 205 and distal femur 207 are resected in a standard manner, the posterior condyles are resected by using a radial resection/sizing guide generally denoted as 200 which is placed onto the distal femur 207. Note the preparation of the femur includes only making the planar distal resection. The radial resection can be centered on the distal femur, or offset from the center line of the femur prior to making the resection in order to account or minimize the amount of medial-lateral translation that can occur during the trialing process as will be discussed below. One method to accomplish the offset is either placing the guide 200 off center, or externally rotating guide 200 prior to pinning to accomplish the offset.

Radial resection/sizing guide 200 is comprised of a cutting block portion 202 having a body 4 which includes a series of guide slots 204 designed to guide a blade runner (a flat metal plate adapted to fit through the sizing guide or cutting guide slots to indicate the resection plane) to size the femur by indicating the approximate level of the anterior resection. Body 4 also includes a guide post 5 extending distally therefrom as well as a series of pinholes 24 for accepting standard bone pins serving to attach and locate body 4 on the distal femur. The central portion of body 4 includes three threaded hole 7, 8 and 9 varying in medial-lateral position to provide different rotational alignments, 0° (neutral), 3° left or 3° right. Obviously other rotational alignments could be provided. An alignment guide 3 may be located on an alignment screw 2 which is threaded into either of hole 7, 8 or 9. If neutral, 3° external rotation (left knee) or 3° external rotation (right knee) is required latch assembly 10 is used to hold guide 3 onto block portion 202. Post 5 is received within U-shaped slot 21 of guide 3. By pressing thumb latch 10' a cam is closed which causes the connection to be co-axial. This is inserted into hole 220 and when released will cause the cam to engage as disclosed in U.S. Publication No. 20060089641, the disclosure of which is incorporated herein by reference. A swing arm 1 which has a bore 206 for slideably receiving post 5 which is preferably cylindrical in shape and has a threaded internal bore (not shown). Swing arm 1 can then be axially locked onto post 5 via threaded thumb screw 6. Obviously threads 208 of thumb screw 6 engage the internal threads of post 5. Swing arm 1 includes a saw blade guide slot 23 which guides a saw blade 280 for resecting the posterior condyles in a single arc as will be described below. Alignment guide 3 also includes skids 22 which engage the posterior condyles for initially locating alignment guide 202. Body 4 also includes a cutout 25 which serves to allow for clearance of the patella and other structures.

Figure 12:
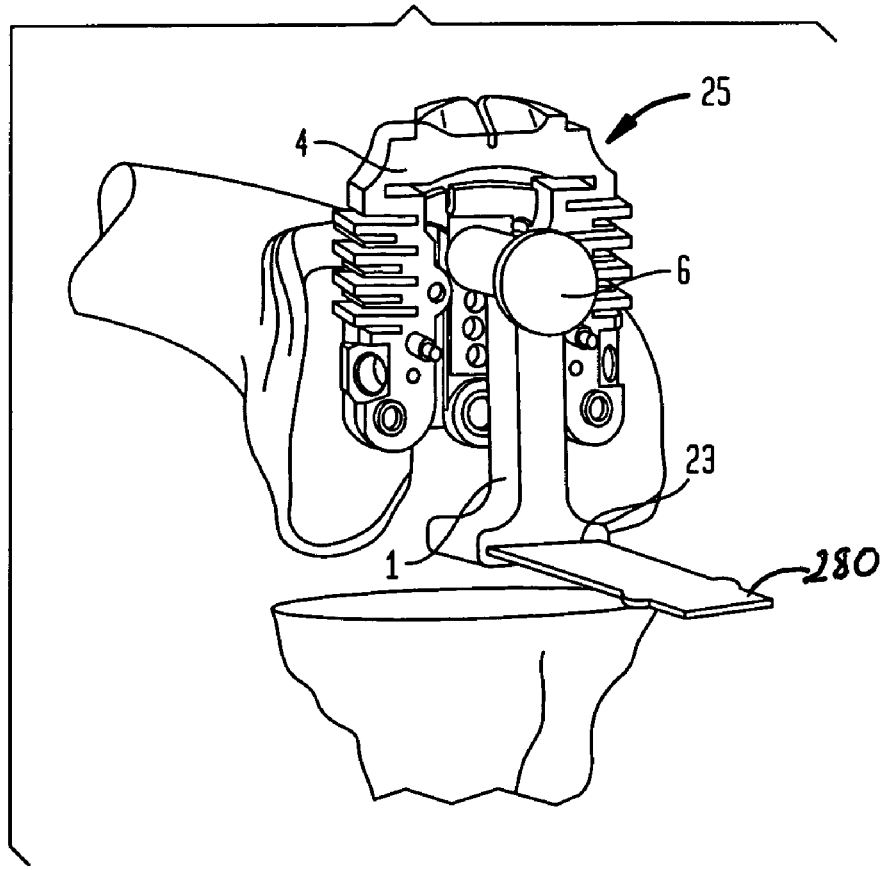
Figure 13:
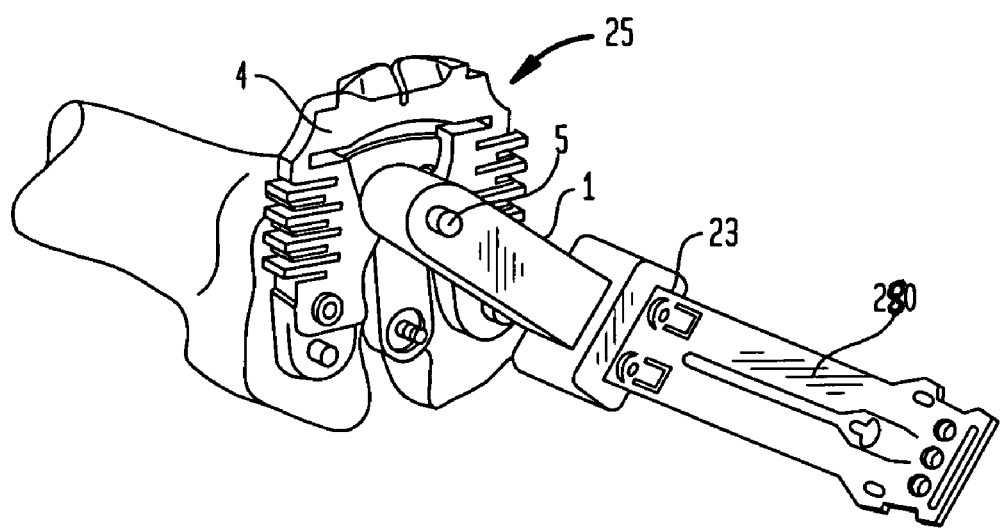
Figure 14:
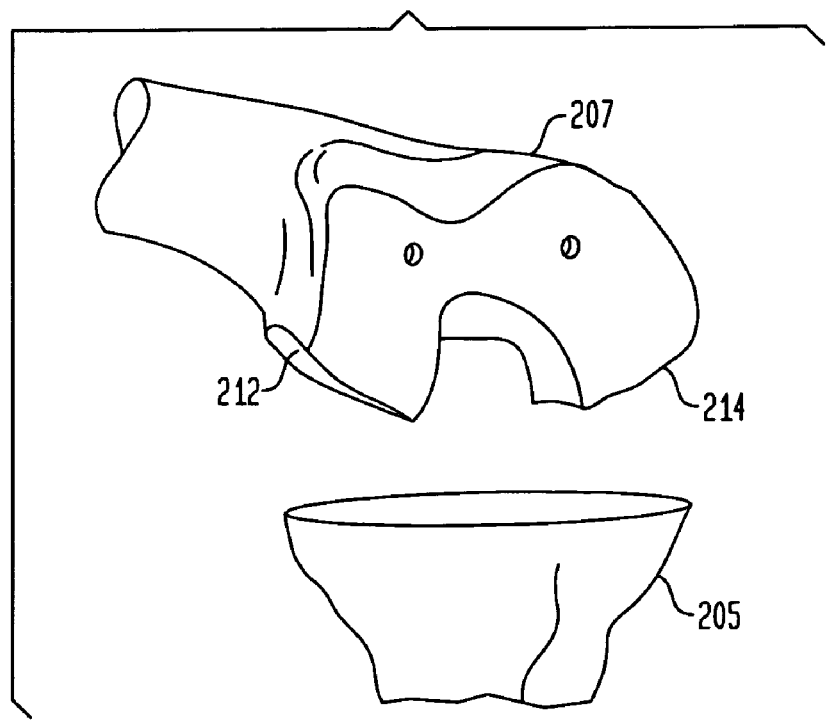

Referring to FIGS. 10 to 13, the skids 22 of guide 3 are placed under the posterior condyles of a femur 207 to set the initial anterior-posterior location of the body 4, as is currently done with standard alignment. Once positioned on the distal femur, the guide 202 can be pinned using pin 209 using any of the holes 24 available. Alignment guide 3 in the preferred embodiment can then be removed by pressing the latch 10 and pulling guide 3 anteriorly with the knee flexed. The swing arm 1 is then placed onto the guide post 5 and the locking thumb screw 6 is assembled to secure the arm in place. As shown in FIGS. 12 and 13, the saw 280 is then inserted into the slot 23 and moved in a pendulum motion to resect the medial and lateral femoral condyles. The resected posterior condyles 212, 214 are shown in FIG. 14. By resecting the condyles individually, the cruciate ligaments can be retained.

Figure 15:
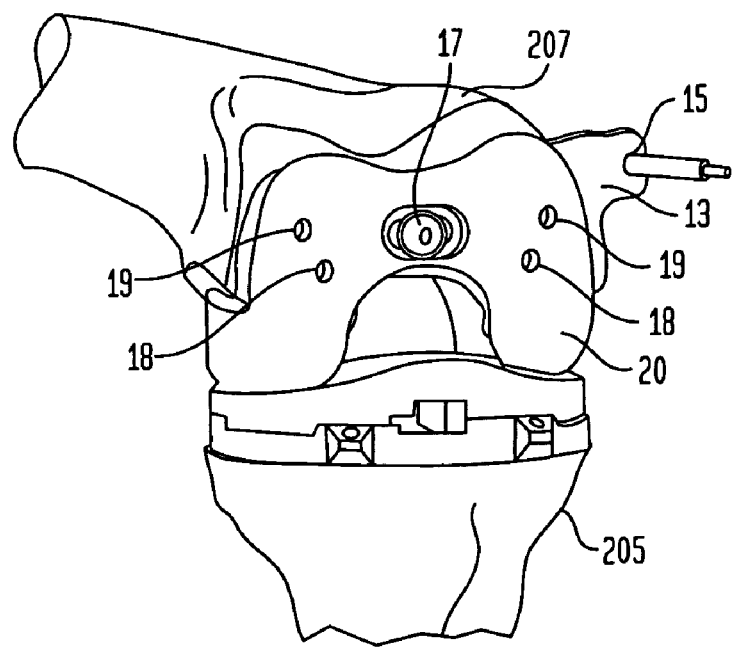

Referring to FIG. 15, the femoral trial assembly 26 of FIGS. 4-7 is then placed onto the resected femur. The locking pins 14 initially will secure the component, and a pin or screw can be inserted through the hole 15 in the shim plate 13 to provide additional stability. The tibial trial (not shown) is then inserted onto tibia 205, and the knee can be taken through a range of motion to allow the navigation system to analyze the alignment of the mechanical axis of the knee, or the normal flexion/extension space balancing can set the components rotation. Once the proper rotation is determined, the outside trial 20 can be pinned through the holes 19, and the two holes 18 can then be drilled to receive pins which locate the resection guide to make the remaining resections on the distal femur such as the anterior and anterior chamfer resections (note the posterior resection does not have to be made). The final step is to implant the component, which has posterior condyles having the same radius as the trial component 20 or 120 to complete implantation.

Figure 18:
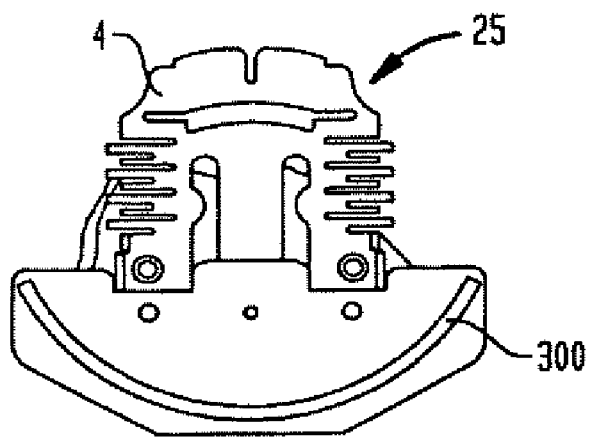
FIG. 18-20 show alternate resection guides for resecting the posterior condyle of the distal femur utilizing the trial instrumentation of the present invention.
Figure 19:
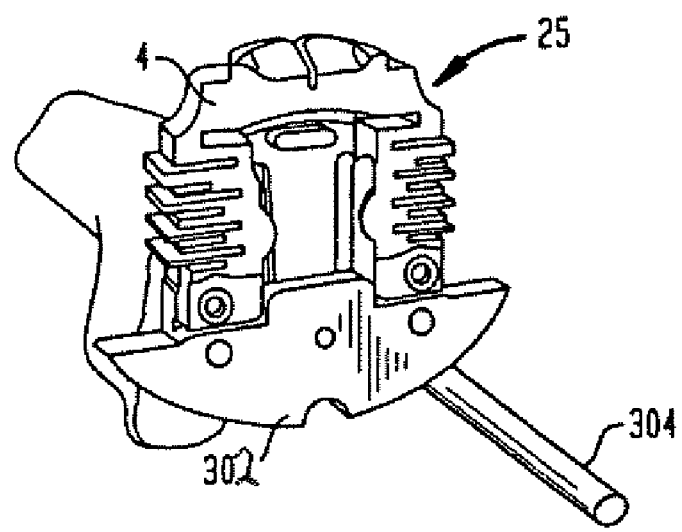
Figure 20:
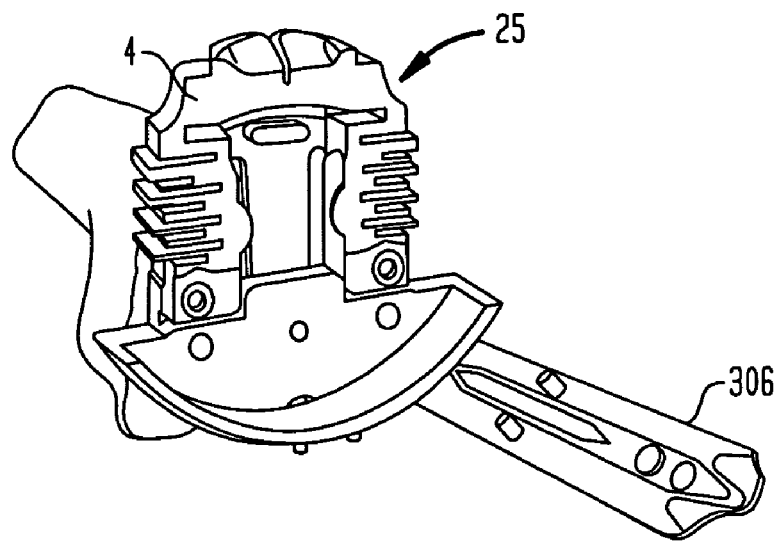
Figure 21:
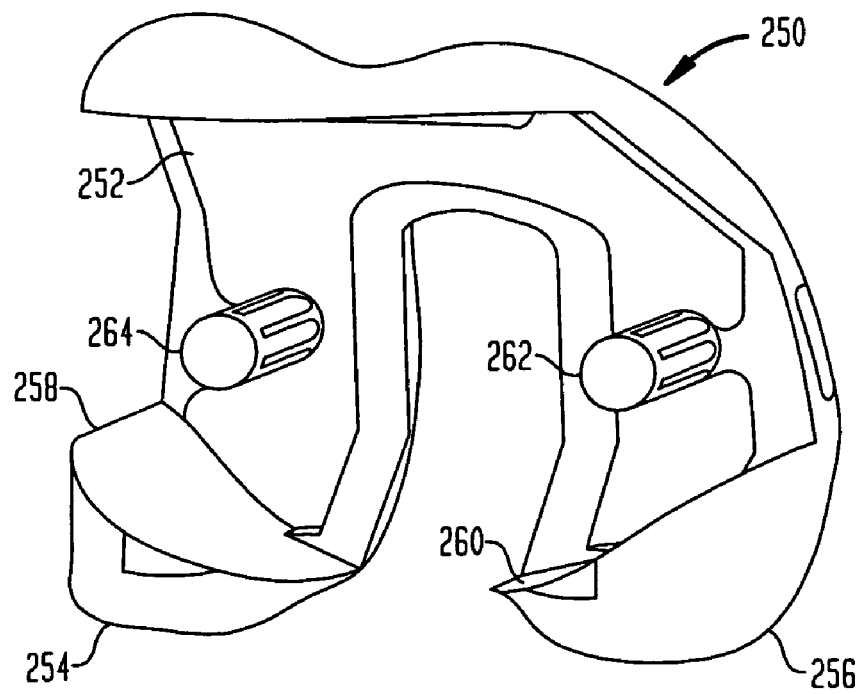
FIG. 21 is a posterior view of the femoral component to be utilized on a distal femur resected utilizing the instrumentation of the present invention.

FIGS. 18-20 show that the arced resection of the posterior condyles can be accomplished in several alternate ways. An offset radial saw, or a circular slot for a burr or saw blade. FIG. 18 shows a curved slot 300 mounted on body 4 of guide 202 for guiding a curved saw blade (not shown). FIGS. 19 and 20 show an arcuate cutting surface 302 which can guide a burr 304 or a curved saw blade 306 as shown in FIG. 20. By placing an oscillating saw like that shown in U.S. Provisional Application No. 60/715,821 through the slot, a radial arc can be created on the posterior condyles. The arcs formed are identical to that of the trial and the prosthesis itself (FIG. 21).

Figure 9A:
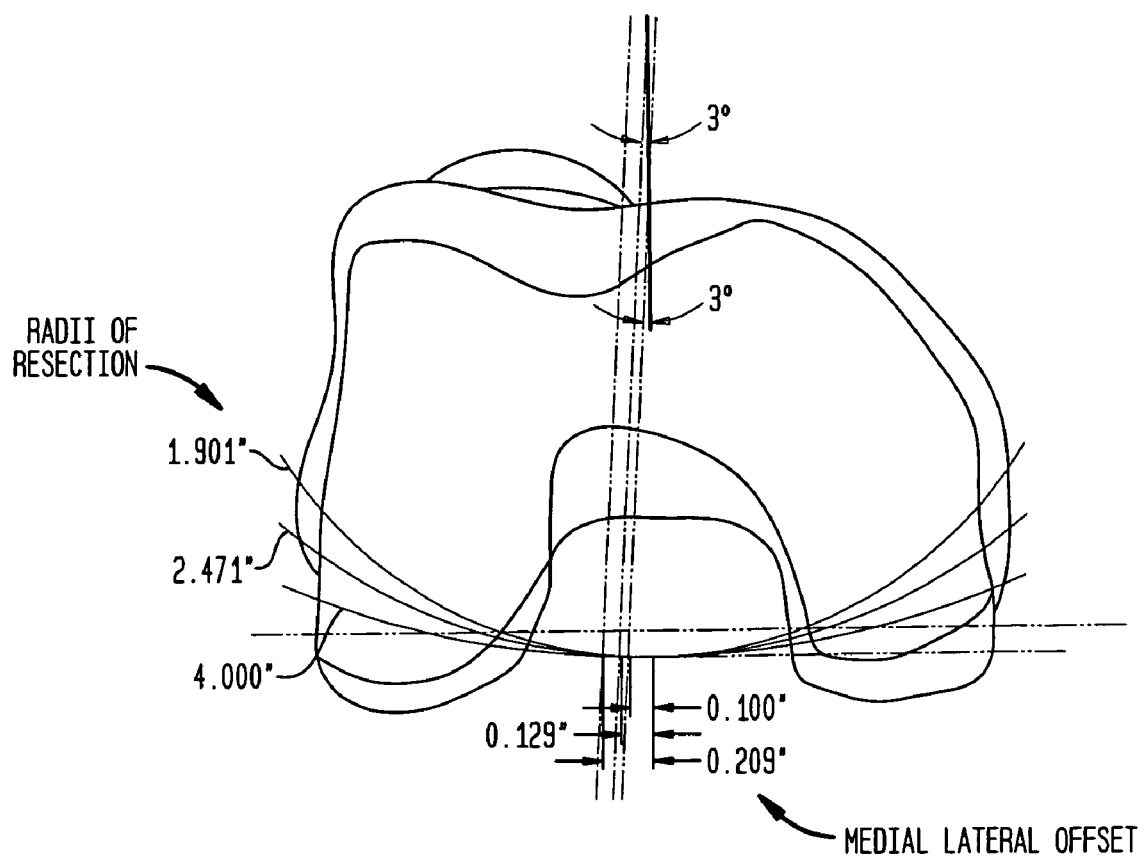
FIG. 9A shows a series of possible resections of the distal femur utilizing the instrument of FIGS. 8 and 9.
Figure 10:
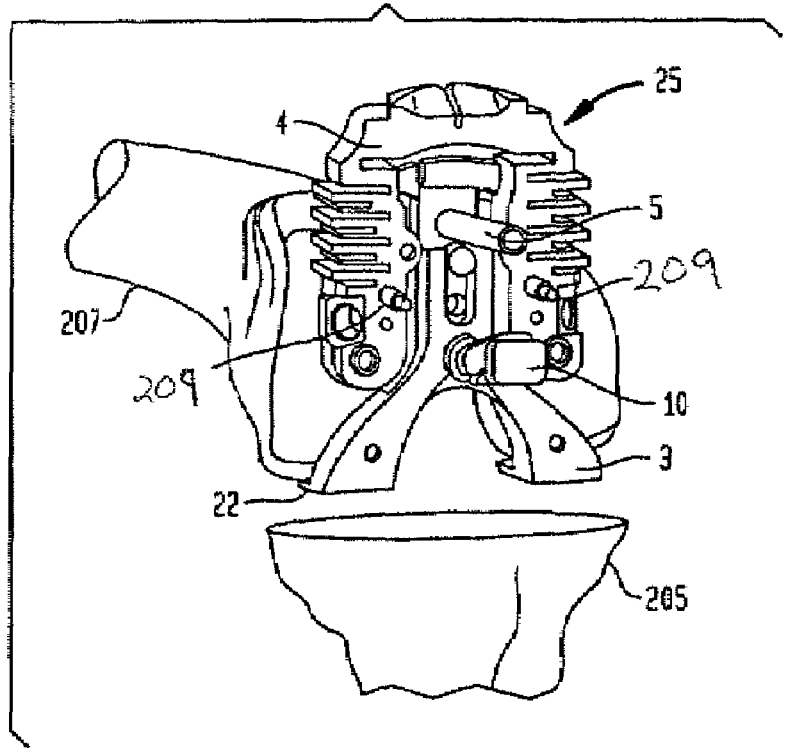
FIGS. 10-17 show the utilization of the instrumentation and alignment guide of the present invention to resect a distal femur.
Figure 11:
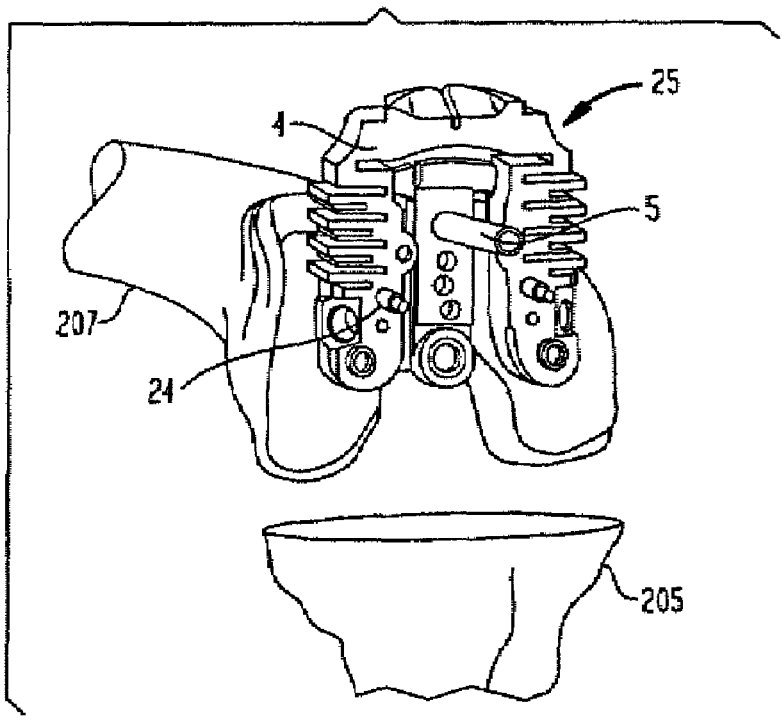

The size of this arc, or the radius, is calculated to provide the minimal amount of medial/lateral femoral shift during the rotation process. FIG. 9A shows a layout of several different radii of curvature. The table below identifies the offset that occurs assuming that approximately 3° of external rotation is average, and the radius of the cut is centered on the knee joint. It is preferred to use a larger radius to remove less bone from the posterior condyles, however, the large shift in positioning is unwanted, so a radius is chosen that is a compromise between the two. It is important to note, that this radius may be optimized for sizes of the femur, either one for all, or one for a group of sizes.

TABLE I

| Radius  | ML Offset       |
|---------|-----------------|
| 1.901"  | 2 mm (.100")    |
| 2.471"  | 3.3 mm (.129")  |
| 4.00"   | 5.4 mm (.209")  |

After the condyles are resected, the trial 20 or 120 is placed and secured to the distal femur as described above. The knee can be taken through a range of motion, and the proper amount of rotation chosen based on a functional analysis obtained from the computer algorithms used with navigation, or simply by ligament tension in the flexed position.

The invention allows the femoral prosthetic rotation to be assessed dynamically, without having to manually advance a mechanism in order to change rotation. In addition, posterior osteophytes can be cleared from the knee, and the arthritic or damaged areas (distal and posterior) be replaced initially with a component.

Referring to FIG. 9A, the numbers in the lower left represent three different radii (approximately 1.9", 2.5" and 4") for the radial resection cut on the posterior condyles. As shown in the figure, a cut along a larger radius (e.g. 4") removes relatively less bone, and a cut along a smaller radius (e.g. 1.9") removes relatively more bone. Based on bone conservation only, a larger radius is more preferable than a smaller radius. A large radius also reduces the risk that the insertion points of the collateral ligaments on the femur will be affected by the radial cut. However, a large radius results in a relatively greater medial-lateral translation for a given femoral component rotation. The amount of M-L translation that results from 3 degrees of rotation is shown in inches in the lower middle of FIG. 9A, and also in mm in column 2 of Table I. Based only on minimizing M-L translation during rotation of the femoral component, a smaller radius is more preferable than a larger radius.

The numbers in the top middle of FIG. 9A all represent the three degrees of external rotation for each of the three different radii cuts shown. The center of rotation for the 4" radius cut is actually somewhere above the figure and not shown in FIG. 9A.

Note that all radial cuts are centered about the Anterior-Poster axis (aka A-P axis or Whiteside's Line).

The optimum radial cut will be one that minimizes bone loss and the risk of cutting the collateral ligament insertion points while at the same time also minimizes M-L translation of the femoral component during rotation of the femoral component. The optimum radius of the radial cut will be a function of anatomy—the optimum radius for small knees will be smaller than the optimum radius for large knees. It is possible to use surgical navigation software to help determine the optimum radius for a radial cut on any particular knee.

Figure 22:
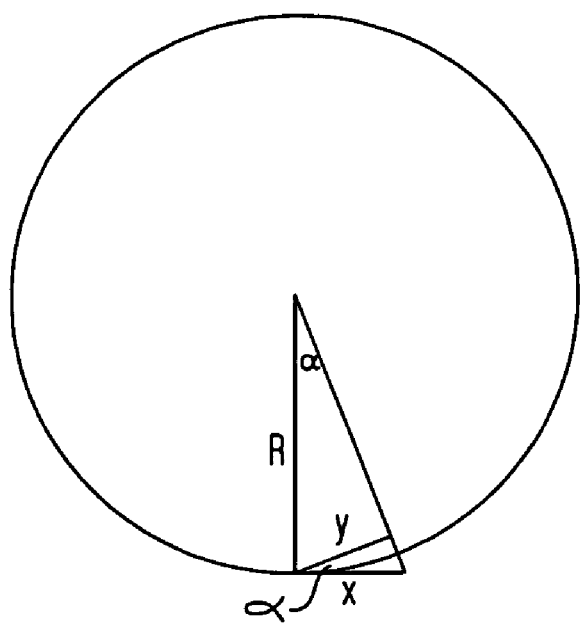
FIG. 22 is a graphical layout of rotation utilized to determine the radius for the posterior condyles.

In the FIG. 22 the variables can be defined as:

R=the radius of the radial resection

X=the linear offset distance from the center of the circle to a point defined by the amount of angular offset or rotation that could occur α=the rotation of the femoral component in degrees that could occur, and Y=the projected medial lateral offset distance that rotation will have on the femoral component.

The value for y or the medial-lateral offset distance that will occur during rotation (preferably less than 3 mm) can be described depending on different radii in the formulas below as derived from FIG. 22 as follows:

$$\tan\alpha = \frac{X}{R}; \text{ and}$$

$$\cos\alpha = \frac{Y}{X}$$

therefore:

$$y = \cos\alpha \tan\alpha R \text{ or}$$

$$R = \frac{Y}{\cos\alpha \tan\alpha}$$

If $y < 3$ mm then $3 > \cos\alpha \tan\alpha R$

Table 2 illustrates which radius values will produce various amounts of medial lateral shifting, depending on the amount of rotation that could be produced.

The goal of the radial resection knee is to provide for ability to rotate femoral component when in flexion to the appropriate degree as determined by dynamic assessment, without dramatically shifting the component medial/lateral away from the knee centerline.

TABLE 2

| y (mm) OFFSET | y (inches) OFFSET | R (mm) | R (inches) |
|---|---|---|---|
| Rotation of 1 degrees | | | |
| 0.0 | 0.000 | 0.00 | 0.000 |
| 0.5 | 0.020 | 28.57 | 1.125 |
| 1.0 | 0.039 | 57.15 | 2.250 |
| 1.5 | 0.059 | 85.72 | 3.375 |
| 2.0 | 0.079 | 114.29 | 4.500 |
| 2.5 | 0.098 | 142.86 | 5.625 |
| 3.0 | 0.118 | 171.44 | 6.750 |
| 3.5 | 0.138 | 200.01 | 7.874 |
| 4.0 | 0.157 | 228.58 | 8.999 |
| 4.5 | 0.177 | 257.16 | 10.124 |
| 5.0 | 0.197 | 285.73 | 11.249 |
| Rotation of 2 degrees | | | |
| 0.0 | 0.000 | 0.00 | 0.000 |
| 0.5 | 0.020 | 14.29 | 0.563 |
| 1.0 | 0.039 | 28.58 | 1.125 |
| 1.5 | 0.059 | 42.87 | 1.688 |
| 2.0 | 0.079 | 57.15 | 2.250 |
| 2.5 | 0.098 | 71.44 | 2.813 |
| 3.0 | 0.118 | 85.73 | 3.375 |
| 3.5 | 0.138 | 100.02 | 3.938 |
| 4.0 | 0.157 | 114.31 | 4.500 |
| 4.5 | 0.177 | 128.60 | 5.063 |
| 5.0 | 0.197 | 142.89 | 5.625 |
| Rotation of 3 degrees | | | |
| 0.0 | 0.000 | 0.00 | 0.000 |
| 0.5 | 0.020 | 9.53 | 0.375 |
| 1.0 | 0.039 | 19.06 | 0.750 |
| 1.5 | 0.059 | 28.58 | 1.125 |
| 2.0 | 0.079 | 38.11 | 1.501 |
| 2.5 | 0.098 | 47.64 | 1.876 |
| 3.0 | 0.118 | 57.17 | 2.251 |
| 3.5 | 0.138 | 66.70 | 2.626 |
| 4.0 | 0.157 | 76.23 | 3.001 |
| 4.5 | 0.177 | 85.75 | 3.376 |
| 5.0 | 0.197 | 95.28 | 3.751 |

Figure 23:
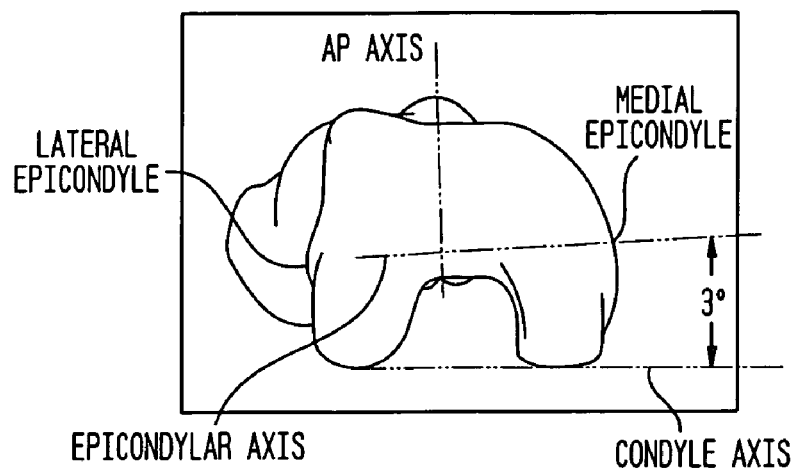
FIG. 23 is a distal view of the femur showing the normal rotational axis for classic resection alignment.
Figure 24:
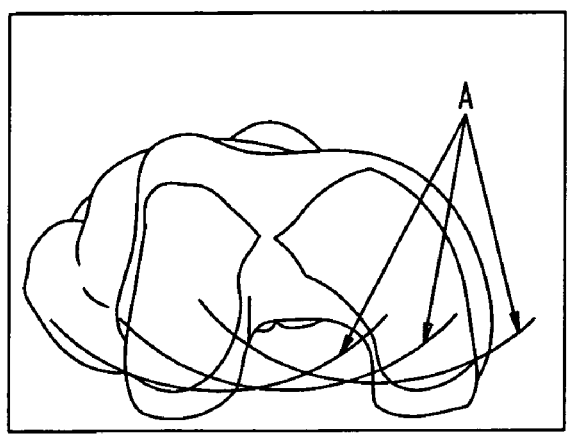
FIG. 24 is an example of several radial positions of the radial cuts based on the medial-lateral position of the resection guide and its angular orientation.

This is accomplished by aligning the radial resection close to the normal rotation of the femur so that the component rotation based on the central axis of the radial cut is closely approximated to the final position (assuming that the "normal" rotation is 3° external). FIG. 23 shows the normal rotation of the femoral component where the AP axis is perpendicular to the epicondylar axis, and final femoral component implantation would be such that the central plane of the femoral component in the sagittal plane is in line or parallel with the AP axis; FIG. 24 shows the effect of not centering the radial cut (cutting guide) on the knee. It shows three curves A depicting radial cuts based on medial-lateral position of the resection guide and angular orientation.

A radius value is chosen and the location on the femoral component for the radial cut which provides for both a minimal amount of offset during rotation and minimal amount of posterior condylar bone removal. The prepared maximum amount of tolerable or justifiable values are: rotation should be 3° and the maximum amount of resultant medial-offset should less than or equal to 3 mm, the radial value from Table 2 above is 2.251". To satisfy the minimal amount of bone removal, the position of the radial resection in the anterior posterior direction (distance from the posterior condylar plane) can be adjusted to achieve the design goal.

Figure 25:
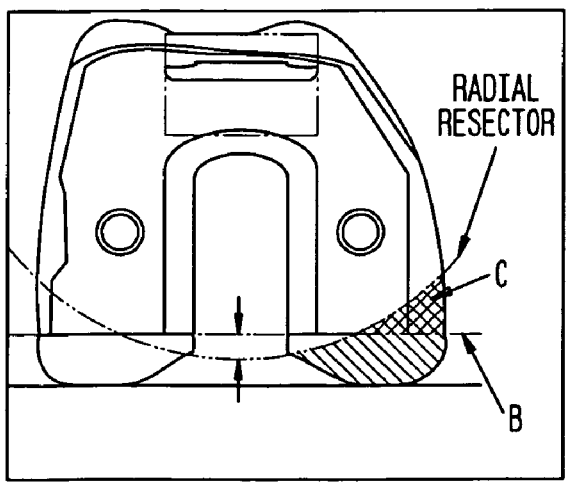
FIG. 25 shows a location of a preferred radial resection.

FIG. 25 shows a radial resection, location B using a standard femoral implant. Current implants have a flat posterior resection level B. By placing the radius on the component, it can easily be seen that there are regions of bone that will be removed from the femur to accommodate the radius. This figure shows an increased amount of bone C over standard (planar resection B) that would be removed.

Figure 26:
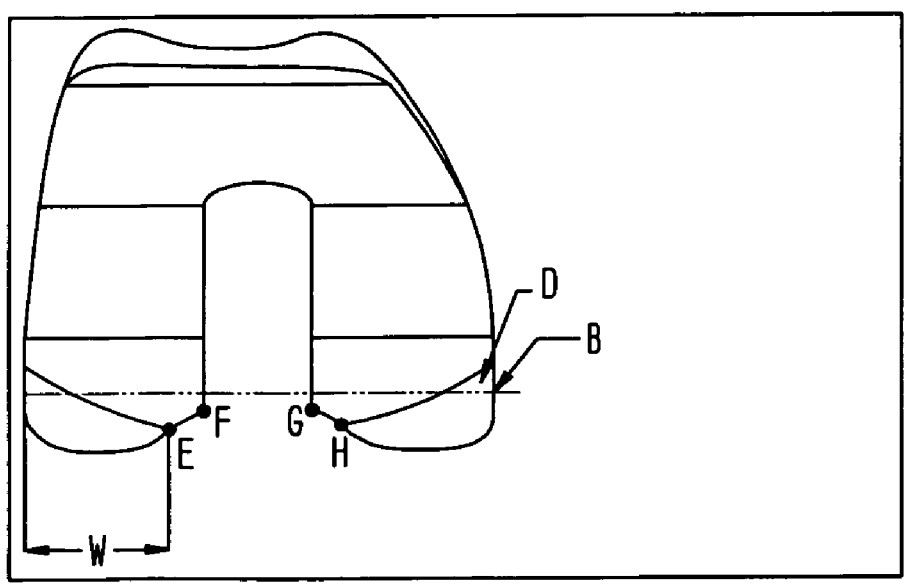
FIG. 26 shows the radius lowered to maintain bone stock.

FIG. 26 shows the radius lowered to a point where the above minimal bone removal goal is achieved, while maintaining a radius that will accommodate the rotation limits (up to 3° beyond the "normal" both internal and external rotation) and no greater than 3 mm of medial-lateral offset at the maximum of 3° additional rotation. The factors that allow this curve to be lowered, is that the curve will pass through points in the femur that define the condylar width W. Condylar width W is further defined as the minimal dimension for a particular femoral component that will maintain the same contact stress levels (area) as originally designed. This defines the center location of the guide post 5 which takes into account for implant design. It moves center point based on distance E-F and G-H. Thus the posterior radius goes through points E and H which minimize the amount of bone removed without reducing load bearing condylar features.

In summary, the location of the radial resection in the medial lateral plane should be located approximately in the location of the center of the knee and parallel to the AP axis of the femur, and its height in the anterior posterior direction is derived from the posterior condylar plane a distance that will maintain the condylar width of the implant design.

The optimum amount of rotation of a femoral component for a particular knee is determined through the use of the knee trials 20, 120 that have been designed to also rotate about the radial cuts made on the posterior condyles.

Figure 16:
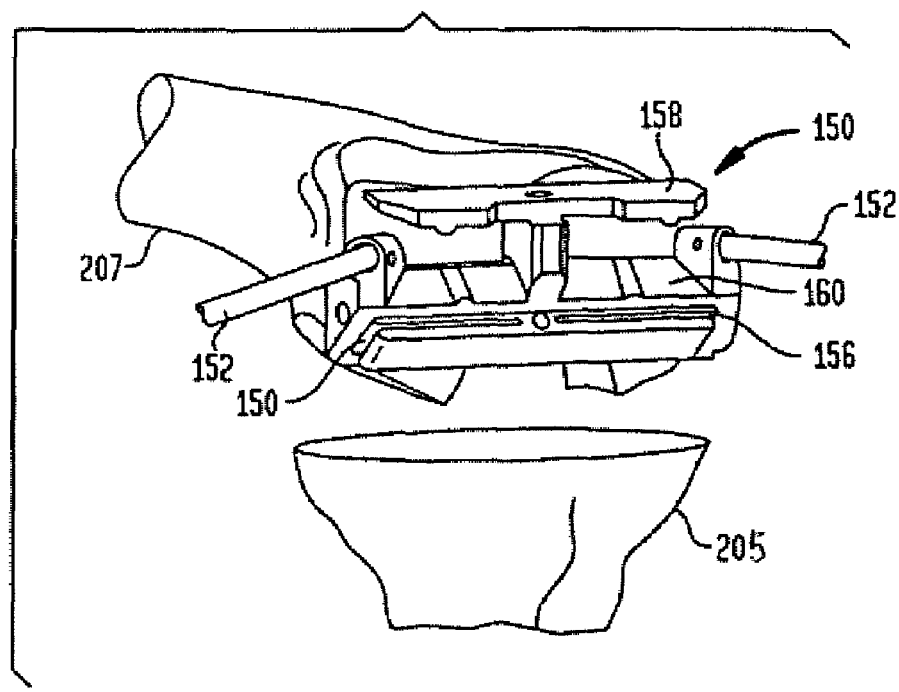
Figure 17:
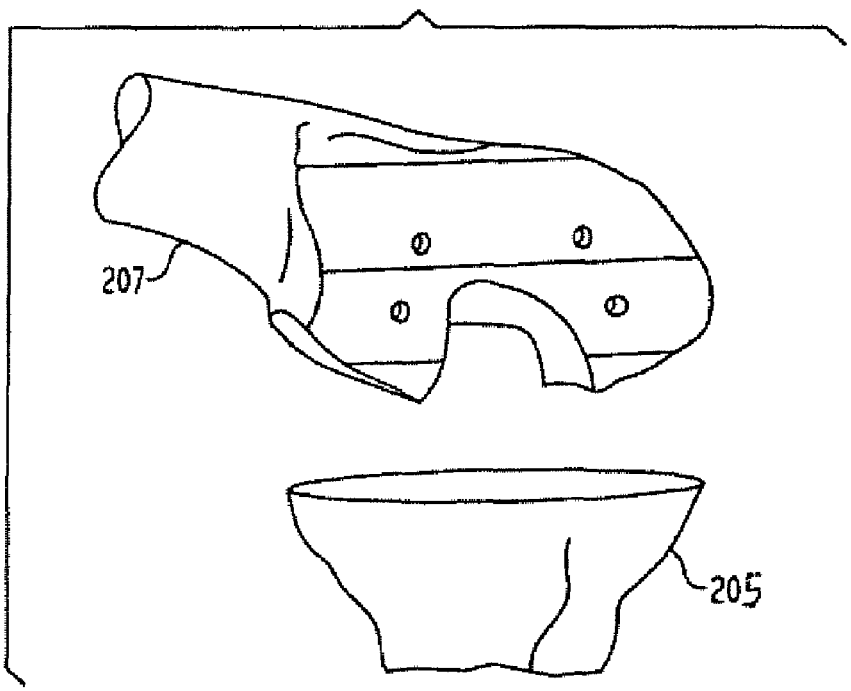

Referring to FIGS. 16 and 17, there is shown a typical femoral cutting block generally denoted as 150 mounted on a resected distal femur 207 by mounting pins 152 as is typical resection guide 150 has a cutting guide slot 156 for making a posterior chamfer cut on the distal femur and a guide surface 158 for making an anterior cut on the distal femur. A cutting guide surface 160 is provided for making an anterior chamfer cut on the distal femoral surface. As shown in FIG. 17, both the resected femur 207 and tibia 205 are shown fully prepared to receive a prosthetic implant on both the femur and tibia.

Referring to FIG. 21, there is a typical femoral implant generally denoted as 250 viewed from its proximal bone contacting side 252 showing the two condylar portions 254 and 256 with the rounded posterior condylar bone contacting surfaces 258 and 260 respectively. As is typical, a pair of bone engaging pins 262 and 264 are provided on the implant 250 for engaging the distal surface of the prepared femur 207. Femoral component 250 may be either attached to the resected distal femur with bone cement or as a press-fit prosthesis using tissue ingrowth.

While a posterior femoral referencing system is disclosed above one skilled in the art would understand that an anterior referencing system could be utilized.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for setting the internal-external rotational position of a prosthetic femoral component with respect to a tibia comprising:

forming a planar surface on a distal surface of a femur;

forming a cylindrical surface on a posterior surface of a femur, said cylindrical surface centered about a first axis extending in a proximal-distal direction with respect to a femur of a knee joint;

placing a template having a planar surface and a cylindrical surface for engaging said cylindrical surface on the posterior surface of the femur against the formed planar surface on the distal surface of the femur with said cylindrical surface in contact with said cylindrical surface on the posterior surface of the femur and the planar surface of the template in contact with the planar surface of the femur, the planar surface of the template extending perpendicular to a central axis of the cylindrical surface of the template; and rotating said template cylindrical surface on said cylindrical surface of the femur about a second axis parallel with the first axis as the knee joint is moved between flexion and extension until the template cylindrical surface is in a position with respect to a tibial condyle surface to properly balance knee ligaments extending between the femur and the tibia.

2. The method as set forth in claim 1 further comprising mounting said template to the formed planar surface of the femur with a first mounting element located on said formed planar surface at an intersection with said second axis.

3. The method as set forth in claim 2 further comprising holding said template in a selected position with a second mounting element.

4. The method as set forth in claim 3 wherein said first mounting element is a bone screw and said second mounting element is a bone pin.

5. The method as set forth in claim 1 wherein said template cylindrical surface has an external shape conforming to the shape of condyles of a prosthetic femoral component.

6. The method as set forth in claim 1 wherein said cylindrical surface of said template has a roller bearing mounted in a recess therein.

7. A method for setting the internal-external rotational position of a prosthetic femoral component with respect to a tibia, comprising:

resecting a distal end of a femur to form a planar distal surface;

placing a cutting guide adjacent the resected distal surface and forming an arcuate surface on a posterior condyle of the femur, the arcuate surface centered about an axis parallel to a proximal-distal axis of the femur of a knee joint;

placing a template having a planar surface and an arcuate guide surface into engagement with the arcuate surface on the posterior condyle of the femur and the planar surface of the template adjacent the planar distal surface of the femur, the planar surface of the template extending perpendicular to a central axis of the arcuate guide surface of the template;

rotating the template arcuate guide surface on the arcuate surface of the posterior condyle about an axis parallel to the central axis while moving the knee joint between flexion and extension until the template arcuate guide surface is in a position with respect to a tibial condyle surface to balance knee ligaments extending between the femur and the tibia; and thereafter resecting an anterior surface of the femur.

8. The method as set forth in claim 7 further comprising mounting said template to the resected planar distal surface of the femur with a first mounting element located on said planar distal surface at an intersection with said axis parallel to said central axis.

9. The method as set forth in claim 8 further comprising holding said template in a selected position with a second mounting element.

10. The method as set forth in claim 9 wherein said first mounting element is a bone screw and said second mounting element is a bone pin.

11. The method as set forth in claim 7 wherein said template arcuate guide surface has an external shape conforming to the shape of condyles of a prosthetic femoral component.

12. The method as set forth in claim 11 wherein said arcuate guide surface of said template has a roller bearing mounted in a recess therein.

13. The method as set forth in claim 7 wherein the axis parallel to the proximal-distal axis is perpendicular to the planar distal surface.

14. A method for setting the internal-external rotational position of a prosthetic femoral component with respect to a tibia, comprising:

resecting a distal end of a femur to form a planar distal surface;

fixing a cutting guide having a body having a planar surface for contacting the planar distal surface of the femur and a cutting guide for forming a cylindrical surface on the distal end of the femur adjacent both a medial and a lateral posterior condyle of the femur;

forming a cylindrical surface on both the medial and lateral posterior condyles by resecting the condyles with the cutting guide;

placing an inner part of a two-part trial on the resected planar distal surface of the femur, the inner part having a cylindrical surface matching the cylindrical surfaces formed on both the medial and lateral posterior condyles; and rotating an outer part of the two-part trial against the inner part and a trial tibial component mounted on a proximal tibia to balance knee ligaments extending between the femur and the tibia to thereby set the desired internal-external rotation of a prosthetic femoral component.

15. The method as set forth in claim 14 further comprising fixing the inner part of the two-part trial on the resected distal end of the femur, the outer part of the two-part trial being mounted on the inner part for rotation about an axis extending perpendicular to the resected planar distal surface of the femur.

16. The method as set forth in claim 15 wherein the axis is approximately parallel with a mechanical axis of the femur.

* * * * *